United States Patent
Greiner et al.

(10) Patent No.: US 6,441,013 B1
(45) Date of Patent: Aug. 27, 2002

(54) SULPHONYLOXAZOLAMINES AS THERAPEUTIC ACTIVE INGREDIENTS

(75) Inventors: Hartmut Greiner, Darmstadt; Gerd Bartoszyk, Weiterstadt; Henning Böttcher; Gerhard Barnickel, both of Darmstadt; Bertram Cezanne, Mörfelden-Walldorf, all of (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/868,097
(22) PCT Filed: Dec. 1, 1999
(86) PCT No.: PCT/EP99/09335
§ 371 (c)(1),
(2), (4) Date: Jun. 14, 2001
(87) PCT Pub. No.: WO00/37452
PCT Pub. Date: Jun. 29, 2000

(30) Foreign Application Priority Data

Dec. 18, 1998 (DE) .......................... 198 58 593

(51) Int. Cl.[7] ..................... A61K 31/42; C07D 263/48; A61P 25/16
(52) U.S. Cl. ..................... 514/376; 514/377; 548/225; 548/233; 548/235
(58) Field of Search ................ 548/225, 233, 548/235; 514/376, 377

(56) References Cited

FOREIGN PATENT DOCUMENTS

WO            9729747            8/1997

OTHER PUBLICATIONS

Chervoni et al Ukr. Khim. Zh. (Russ. Ed.) 1991, 57 (4), 415–18 CAS Abstract.*
Chemical Abstracts vol. 118 No. 125087 (Mar. 2, 1993) abstract No. 124426 p. 798.

Chervonyi, V.A. et al: "Cyclocondensation of N–(1–arylsulfo–1,2,3–dichlorethynyl)amides of carbonic acids with amines and sodium hyrosulfide" UKR.KHIM.ZH. vol. 57 No. 4 1991.

* cited by examiner

Primary Examiner—Joseph K. McKane
Assistant Examiner—Kamal Saeed
(74) Attorney, Agent, or Firm—Millen, White, Zelano & Branigan, P.C.

(57) ABSTRACT

The present invention relates to sulphonylexazolamines of general formula (I), wherein $R^1$, $R^2$ represent independently from each other H, A, —$(CH_2)_n$—Ar or alkenyl with 2–6 C atoms, $R^1$ and $R^2$ together also represent a mononuclear saturated heterocycle with 1–2 N, O and/or S atoms, Z is H, A, $CF_3$, $NO_2$, Hal, OH, OA, $NH_2$, NHA or $NH_2$. A represents alkyl with 1–6 C atoms, Ar is Z-monosubstituted or Z-disubstituted phenyl, Hal is F, Cl, Br, or L n is 1 or 2 of the physiologically acceptable salts or solvates thereof. Said sulphonyloxazolamines are used as therapeutic active ingredients. The invention also relates to the use of sulphonyloxazolamines as therapeutic active ingredients and/or to the production of pharmaceutical preparations to combat diseases of the central nervous system. The invention further relates to a pharmaceutical preparation and the production thereof.

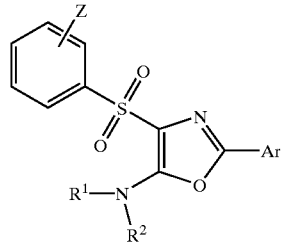

(I)

7 Claims, No Drawings

SULPHONYLOXAZOLAMINES AS THERAPEUTIC ACTIVE INGREDIENTS

This application is a 371 of PCT/EP99/09335 filed on Dec. 1, 1999.

The invention relates to sulfonyloxazolamines of the general formula I

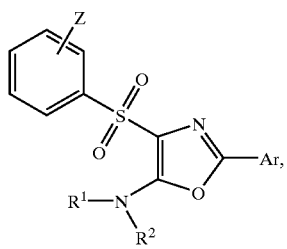

in which

R$^1$, R$^2$ each independently of one another are H, A, —(CH$_2$)$_n$—Ar or alkenyl having 2 to 6 C atoms, R$^1$ and R$^2$ together are also a mononuclear saturated heterocycle having 1 to 2 N, O and/or S atoms, Z, is H, A, CF$_3$, NO$_2$, Hal OH, OA, NH$_2$, NHA or NA$_2$, A is alkyl having 1 to 6 C atoms, Ar is phenyl which is mono- or di-substituted by Z, Hal is F, Cl, Br or I, n is 1 or 2, or their physiologically acceptable salts or solvates as therapeutic active compounds.

The invention furthermore relates to the use of the sulfonyloxazolamines of the general formula I as therapeutic active compounds.

The invention also relates to the use of the sulfonyloxazolamines of the general formula I for the production of pharmaceutical preparations in the control of disorders of the central nervous system.

Some compounds of the general formula I are known from various earlier publications. Thus, the preparation of the compounds of the formula I is described in V. A. Chervonyi et al., *Ukr. Khim. Zh.* (Russ. Ed.) 1991, 57(4), 415–418 or V. A. Chervonyi et al., *Zh. Org. Khim.* 1988, 24 (2), 453–4 corresponding to V. A. Chervonyi et al., *J. Org. Chem. USSR* (Engl. transl.) 1988, 24, 401. More detailed publications with respect to the pharmacological efficacy of the compounds of the formula I are not available in the prior art.

The invention was based on the object of finding novel useful properties of sulfonyloxazolamines, in particular those which confirm the compounds to be therapeutic active compounds and/or can lead to the use of the sulfonyloxazolamines as therapeutic active compounds and/or to the production of pharmaceutical preparations.

It has been found that the compounds of the formula I and their pharmacologically active salts surprisingly have a selective affinity for 5-HT6 receptors, together with good tolerability. They exhibit 5-HT6-antagonistic or 5-HT6 agonistic actions.

5-HT6 receptors form a subfamily of 5-HT receptors. The neurotransmitter 5-hydroxytryptamine (5-HT), also known as serotonin, is an important regulating neurotransmitter in the brain, whose actions are assisted by a a family of receptors which, at the current level of knowledge, contain 13 G protein-coupled receptors and an ion channel.

The greatest density of the serotonin S-HT6 receptors in the brain is found in the olfactory tubercle, in the nucleus accumbens, in the striatum, in the dentate gyrus and in the CA1–3 regions of the hippocampus. These regions are involved to a particular extent in psychiatric disorders such as, for example, schizophrenia or depression. Moreover, At is known from animal experiments that the administration ox 5-HT6 antisense oligonucleotides causes a behavioural syndrome which corresponds to that of dopamine agonists. Furthermore, hyperactivity of the dopaminergic neurotransmitter system in schizophrenia (dopamine hypothesis of schizophrenia) is pathophysiologically confirmed. However, dysfunctions of the dopamine system in various forms of depression have been demonstrated. Of the established or alternatively newer therapeutics which are employed in clinical practice for the treatment of these psychiatric disorders, a large number moreover bind to the 5-HT6 receptor. The atypical neuroleptics (e.g. clozapine) and the tricyclic antidepressants (e.g. amitriptyline) may be mentioned here in particular.

Moreover, it was found in animal experimental investigations that 5-HT6 receptors in the brain control cholinergic neurotransmission. Cholinergics are employed in disorders with memory disturbances such as, for example, Alzheimer's disease.

For these reasons, it can be concluded that there is an involvement of the 5-HT6 receptor in psychiatric and neurological disorders such as, preferably, schizophrenia, depression and Alzheimer's.

The compounds of the formula I and their physiologically acceptable salts are therefore suitable as therapeutic active compounds for disorders of the central nervous system. The compounds of the formula I and their physiologically acceptable salts or solvates are particularly suitable for the treatment of psychoses, schizophrenia, manic depression (B. L. Roth et al., *J. Pharmacol. E. Ther.* 1994, 268, 1403–1410), depression (D. R. Sibley et al., *Mol. Pharmacol.* 1993, 43, 320–327), neurological disorders (A. Bourson et al., *J. Pharmacol. Exp. Ther.* 1995, 274, 173–180), memory disorders, Parkinson's disease, amyotrophic lateral sclerosis, Alzheimer's disease, Huntington's disease (A. J. Sleight et al., *Neurotransmissions* 1995, 11, 1–5), bulimia, anorexia nervosa or other eating disorders, compulsive acts or of premenstrual syndrome.

The invention relates to the compounds of the formula I or their physiologically acceptable salts or solvates as therapeutic active compounds.

The invention relates to the use of compounds of the formula I or their physiologically acceptable salts or solvates as therapeutic active compounds.

The invention furthermore relates to the use of compounds of the formula I or their physiologically acceptable salts or solvates as therapeutic active compounds or disorders of the central nervous system.

Solvates of the compounds of the formula I are understood as meaning adducts of inert solvent molecules to the compounds of the formula I, which are formed on account of their mutual force of attraction. Solvates are, for example, mono- or dihydrates or alcoholates.

For all radicals which occur more than once, such as, for example, Z, it holds true that their meanings are independent of one another.

Above and below, the radicals and parameters R$^1$, R$^2$, Z and n have the meanings indicated in the formulae I to VI, if not expressly stated otherwise.

In the above formulae, A is alkyl, is linear or branched, and has 1 to 6, preferably 1, 2, 3 or 4, C atoms. A is preferably methyl, furthermore ethyl, propyl, butyl, isobutyl, sec-butyl or tert-butyl, in addition also pentyl, 1-, 2- or 3-methylbutyl, 1,1-, 1,2- or 2,2-dimethylpropyl, 1-ethylpropyl or hexyl. Methyl is particularly preferred.

Alkenyl is preferably allyl, 2- or 3-butenyl, isobutenyl, sec-butenyl, in addition is preferably 4-pentenyl, isopentenyl or 5-hexenyl. Allyl is particularly preferred for alkenyl.

Ar is preferably phenyl which is mono- or disubstituted by Z, where Z can be X, A, $CF_3$, $NO_2$, Hal, OH, OA, $NE_2$, NHA or $NA_2$.

Ar is therefore preferably phenyl, o-, m- or p-methylphenyl, o-, m- or p-ethylphenyl, o-, m- or p-propylphenyl, o-, m- or p-isopropylphenyl, o-, m- or p-ter-butylphenyl, o-, m- or p-aminophenyl, o-, m- or p-N,N-dimethylaminophenyl, o-, m- or p-nitrophenyl, o-, m- or p-hydroxyphenyl, o-, m- or p-methoxyphenyl, o-, m- or p-ethoxyphenyl, o-, m-, p-trifluoromethylphenyl, o-, m- or p-fluorophenyl, o-, m- or p-chlorophenyl, o-, m- or p-bromopheryl, furthermore preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl.

Phenyl, o- or p-methylphenyl, o- or p-chlorophenyl, p-bromophenyl, p-methoxyphenyl or 2,4-dichlorophenyl is particularly preferred for Ar.

In —$(CH_2)_n$—Ar, Ar has one of the preferred meanings indicated beforehand, where n can be 1 or 2. Benzyl is particularly preferred for —$(C_2)_n$—Ar.

Hal is preferably fluorine, chlorine or bromine.

Z is H, A, $CF_3$, $NO_2$, Hal, OH, OA, $NH_2$, NHA or $NA_2$, where A and Hal have one of the preferred meanings indicated beforehand. H, methyl, chlorine, bromine or methoxy is particularly preferred for Z.

n is preferably 1 or 2, particularly preferably 1.

$R^1$ and $R^2$ are, independently of one another, H, A —$(CH_2)_n$—Ar or alkenyl having 2 to 6 C atoms, where A, Ar, alkenyl and n have one of the, preferred or particularly preferred meanings indicated beforehand.

In addition, $R^1$ and $R^2$ together are also a mononuclear saturated heterocycle having 1 to 2 N, O and/or S atoms.

$R_1$ and $R^2$ together are preferably tetrahydro-2- or -3-furyl, 1,3-dioxolan-4-yl, tetrahydro-2- or -3-thienyl, 1-, 2- or 3-pyrrolidinyl, tetrahydro-1-, -2- or -4-imidazolyl, tetrahydro-1-, -3- or -4-pyrazolyl, 1-, 2-, 3- or 4-piperidinyl, 1-, 2-, 3- or 4-perhydroazepinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl or 1-, 2- or 3-piperazinyl. 1-Piperidinyl or 4-morpholinyl is particularly preferred for $R^1$ and $R^2$ together.

For the subject of the invention, of the therapeutic active compounds of the formula I or their physiologically acceptable salts or solvates, of the use of the compounds of the formula I or their physiologically acceptable salts or solvates as therapeutic active compounds or of the production of a pharmaceutical preparation for the treatment of disorders of the central nervous system, in particular those compounds of the formula I are preferred in which at least one of the radicals mentioned has one of the preferred or particularly preferred meanings indicated above. Some preferred groups of compounds can be expressed by the following subformulae Ia to Ic, which correspond to the formula I and in which the radicals not described in greater detail have the meaning indicated in the formula I, but in which in Ia $R^1$ and $R^2$ in each case independently of one another are H, A, —$(CH_2)_n$—Ar or alkenyl having 2 to 6 C atoms;

in Ib $R^1$ and $R^2$ in formula I together are 1-piperidinyl;

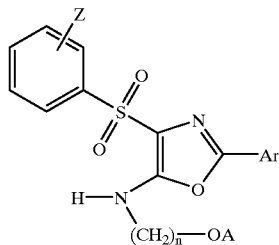

or in Ic $R^1$ and $R^2$ in formula I together are 4-morpholinyl;

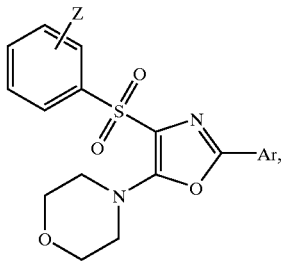

The following compounds of the formulae Ia, Ib and Ic are particularly preferred for use according to claim 1:

dimethyl-[2-phenyl-4-(toluene-4-sulfonyl)oxazol-5-yl]-amine;

[2-(2,4-dichlorophenyl)-4-(toluene-4-sulfonyl)oxazol-5-yl]dimethylamine;

benzyl-[2-(2,4-dichlorophenyl)-4-(toluene-4-sulfonyl)-oxazol-5-yl]amine;

methyl-[4-(toluene-4-sulfonyl)-2-p-tolyloxazol-5-yl]amine;

benzyl-[4-(4-chlorobenzenesulfonyl)-2-(2,4-dichlorophenyl)oxazol-5-yl]amine;

(4-benzenesulfonyl-2-m-tolyloxazol-5-yl)benzylamize;

[4-(4-chlorobenzenesulfonyl)-2-p-tolyloxazol-5-yl]-dimethylamine;

(4-benzenesulfonyl-2-o-tolyloxazol-5-yl)methylamine;

benzyl-[4-(4-chlorobenzenesulfonyl)-2-(2-chlorophenyl)-oxazol-5-yl]amine;

[4-benzenesulfonyl-2-(2,4-dichlorophenyl)oxazol-5-yl]-benzylamine;

[4-benzenesulfonyl-2-(2,4-dichlorophenyl)oxazol-5-yl]-dimethylamine;

[4-benzenesulfonyl-2-(2-chlorophenyl)oxazol-5-yl]-dimethylamine;

1-[2-(2,4-dichlorophenyl)-4-(toluene-4-sulfonyl)-oxazol-5-yl]piperidine;

1-[4-benzenesulfonyl-2-(2,4-dichlorophenyl)oxazol-5-yl]piperidine;

1-[4-benzenesulfonyl-2-(2-chlorophenyl)oxazol-5-yl]-piperidine;

4-[4-(toluene-4-sulfonyl)-2-p-tolyloxazol-5-yl]-morpholine;

4-[4-(4-chlorobenzenesulfonyl)-2-p-tolyloxazol-5-yl]-morpholine;

4-[4-(4-chlorobenzenesulfonyl)-2-phenyloxazol-5-yl]-morpholine;

4-[4-(4-benzenesulfonyl)-2-(4-bromophenyl)oxazol-5-yl]-morpholine;
4-[4-(4-benzenesulfonyl)-2-m-tolyloxazol-5-yl]-morpholine;
4-[4-(4-benzenesulfonyl)-2-(4-methoxyphenyl)oxazol-5-yl]morpholine;
4-[4-(4-benzenesulfonyl)-2-phenyloxazol-5-yl]-morpholine;
allyl-(4-benzenesulfonyl-2-phenyloxazol-5-yl)amine,
4-[4-benzenesulfonyl-2-(2-chlorophenyl)oxazol-5-yl]-morpholine;
(4-benzenesulfonyl-2-phenyloxazol-5-yl)dimethylamine;
(4-benzenesulfonyl-2-m-tolyloxazol-5-yl)dimethylamine;
benzyl-[2-phenyl-4-(toluene-4-sulfonyl)oxazol-5-yl]-amine and
benzyl-[4-(toluene-4-sulfonyl)-2-m-tolyloxazol-5-yl]-amine.

In relation to formula Ia, the following known compounds are preferred for use as therapeutic active compounds:
dimethyl-[2-phenyl-4-(toluene-4-sulfonyl)oxazol-5-yl]-amine;
[2-(2,4-dichlorophenyl)-4-(toluene-4-sulfonyl)oxazol-5-yl]dimethylamine;
benzyl-[2-(2,4-dichlorophenyl)-4-(toluene-4-sulfonyl)-oxazol-5-yl]amine;
methyl-[4-(toluene-4-sulfonyl)-2-p-tolyloxazol-5-yl]-amine;
benzyl-[4-(4-chlorobenzenesulfonyl)-2-(2,4-dichlorophenyl)oxazol-5-yl]amine;
(4-benzenesulfonyl-2-m-tolyloxazol-5-yl)benzylamine;
[4-(4-chlorobenzenesulfonyl)-2-p-tolyloxazol-5-yl]-dimethylamine;
(4-benzenesulfonyl-2-o-tolyloxazol-5-yl)methylamine;
benzyl-[4-(4-chlorobenzenesulfonyl)-2-(2-chlorophenyl)-oxazol-5-yl]amine;
[4-benzenesulfonyl-2-(2,4-dichlorophenyl)oxazol-5-yl]-benzylamine;
allyl-(4-benzenesulfonyl-2-phenyloxazol-5-yl)amine;
(4-benzenesulfonyl-2-phenyloxazol-5-yl)dimethylamine;
(4-benzenesulfonyl-2-m-tolyloxazol-5-yl)dimethylamine;
benzyl-[2-phenyl-4-(toluene-4-sulfonyl)oxazol-5-yl]-amine;
benzyl-[4-(toluene-4-sulfonyl)-2-m-tolyloxazol-5-yl]-amine;
[4-benzenesulfonyl-2-(2,4-dichloropnenyl)oxazol-5-yl]dimethylamine and
[4-benzenesulfonyl-2-(2-chlorophenyl)oxazol-5-yl]dimethylamine.

In relation to formula Ib, the following known compounds are preferred for use as therapeutic active compounds:
1-[2-(2,4-dichlorophenyl)-4-(toluene-4-sulfonyl)-oxazol-5-yl]piperidine;
1-[4-benzenesulfonyl-2-(2,4-dichlorophenyl)oxazol-5-yl]piperidine and
1-[4-benzenesulfonyl-2-(2-chlorophenyl)oxazol-5-yl]piperidine.

In relation to formula Ic, the following known compounds are preferred for use as therapeutic active compounds:
4-[4-(toluene-4-sulfonyl)-2-p-tolyloxazol-5-yl]-morpholine;
4-[4-(4-chlorobenzenesulfonyl)-2-p-tolyloxazol-5-yl]-morpholine;
4-[4-(4-chlorobenzenesulfonyl)-2-phenyloxazol-5-yl]-morpholine;
4-[4-(4-benzenesulfonyl)-2-(4-bromophenyl)oxazol-5-yl] morpholine;
4-[4-(4-benzenesulfonyl)-2-m-tolyloxazol-5-yl]-morpholine;
4-[4-benzenesulfonyl-2-(2-chlorophenyl)oxazol-5-yl]-morpholine;
4-[4-(4-benzenesulfonyl)-2-(4-methoxyphenyl)oxazol-5-yl]morpholine and
4-[4-(4-benzenesulfonyl)-2-phenyloxazol-5-yl]-morpholine.

The invention furthermore relates to the use of the following compounds, selected from the group
a) dimethyl-[2-phenyl-4-(toluene-4-sulfonyl)oxazol-5-yl]amine,
b) [2-(2,4-dichlorophenyl)-4-(toluene-4-sulfonyl)-oxazol-5-yl]dimethylamine,
c) benzyl-[4-(4-chlorobenzenesulfonyl)-2-(2-chlorophenyl)oxazol-5-yl]amine,
d) (4-benzenesulfonyl-2-o-tolyloxazol-5-yl)-methylamine,
e) benzyl-[2-(2,4-dichlorophenyl)-4-(toluene-4-sulfonyl)oxazol-5-yl]amine,
f) [4-benzenesulfonyl-2-(2,4-dichlorophenyl)oxazol-5-yl]benzylamine,
g) [4-benzenesulfonyl-2-(2,4-dichlorophenyl)oxazol-5-yl]dimethylamine,
or one of their physiologically acceptable salts or solvates as therapeutic active compounds against disorders of the central nervous system.

The compounds of the formula I are generally commercially obtainable or can be synthesized according to the following synthesis scheme (for this cf. V. A. Chervonyi et al., *Ukr. Khim. Zh.* (Russ. Ed.) 1991, 57(4), 415–418 or V. A. Chervonyi et al., *Zh. Org. Khim.* 1988, 24(2), 453–4, corresponding to V. A. Chervonyi et al., *J. Org. Chem. USSR* (Engl. transl.) 1988, 24, 401).

Synthesis scheme :

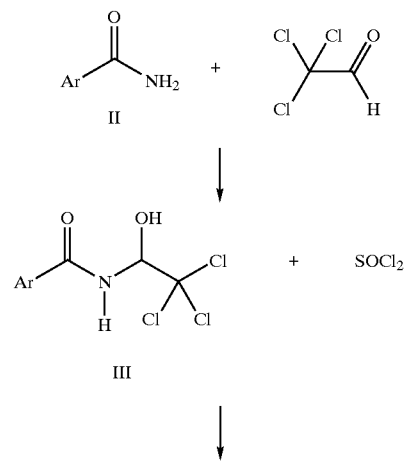

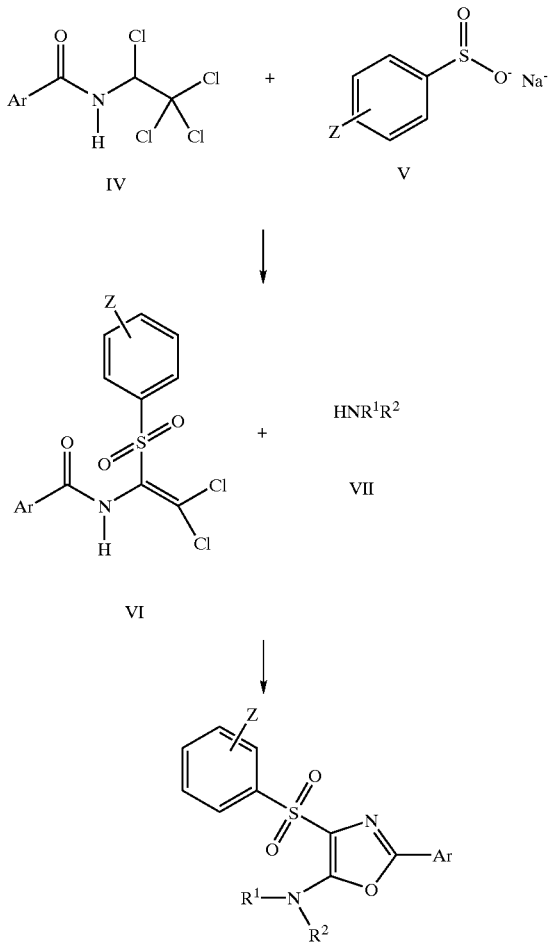

In the synthesis scheme shown beforehand, the starting material of the formula II is reacted with trichloroacetate to give the compound III. The reaction with thionyl chloride and subsequently with the sodium sulfinate of the formula V generates an aryl vinyl sulfone of the formula VI, which cyclizes to give the sulfonyloxazolamines of the formula I by reaction with an amine of the formula VII. In this connection, the substituents Ar, Z, $R^1$ and $R^2$ of the formula II to VII have preferred or particularly preferred meanings as indicated beforehand.

The suitable reaction conditions of the reactions mentioned from the synthesis scheme are known from the references V. A. Chervonyi et al., *Ukr. Khim. Zh.* (Russ. Ed.) 1991, 57(4), 415–418 or V. A. Chervonyi et al., *Zh. Org. Khim.* 1988; 24(2), 453–4 corresponding to V. A. Chervonyi et al., *J. Org. Chem. USSR* (Engl. transl.) 1988, 24, 401, or from standard works such as, for example, Houben-Weyl, Methoden der organischen Chemie [Methods of organic Chemistry], Georg-Thieme-Verlag, Stuttgart. In this case, use can also be made of variants which are known per se, but not mentioned here in greater detail.

A base of the formula I can be converted into the associated acid addition salt using an acid, for example by reaction of equivalent amounts of the base and of the acid in an inert solvent such as ethanol and subsequent evaporation. For this reaction, suitable acids are in particular those which yield physiologically acceptable salts. Thus inorganic acids can be used, e.g. sulfuric acid, nitric acid, hydrohalic acids such as hydrochloric acid or hydrobromic acid, phosphoric acids such as orthophosphoric acid, sulfamic acid, in addition organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, p-toluenesulfonic acid, naphthalenemono- and disulfonic acids or lauryl sulfuric acid. Salts with physiologically unacceptable acids, e.g. picrates, can be used for the isolation and/or purification of the compounds of the formula I.

The binding of the compounds of the formula I to 5-HT6 receptors was determined as follows: The substances to be tested were dissolved in DMSO at a concentration of 1 mM and diluted to the desired concentrations (0.1 nM to 10 $\mu$M) using test buffer (20 mM HEPES, 0.1% ascorbic acid, adjusted to pH 7.4 using NaOH).

20 $\mu$l of the respective substance solution were incubated at 37° C. for 1 hour with 80 $\mu$l of $^3$H-LSD solution (TRK-1041, Amersham Pharmacia, Freiburg, spec. act. 80–90 Ci/mMol, 1 nM in the batch) and 100 $\mu$l of membrane suspension (5-HT6 receptors, RB-HS6, Biotrend, Cologne, 25–30 $\mu$g of protein). The reaction mixture was filtered through GFB Filters (Whatman) which had been pretreated with 0.1% aqueous polyethyleneimine solution for 1 hour. The filters were washed 3 times with 3 ml of test buffer, the filters [sic] transferred to minivials and, after addition of Ultima Gold (Packard, Frankfurt), the radioactivity was determined in a liquid scintillation counter. The evaluation and $IC_{50}$ determination was carried out by means of in-house programs in RS1 (BBN Software Corporation).

The compounds of the formula I have a selective affinity for 5-HT6 receptors having an inhibition constant $IC_{50}$ of less than 4 $\mu$mol/l.

The invention furthermore relates to the use of the compounds of the general formula I for the production of a pharmaceutical preparation for controlling disorders of the central nervous system.

The invention furthermore relates to the use of compounds of the general formula I for the production of a pharmaceutical preparation for the treatment of psychoses, schizophrenia, manic depression, depression, neurological disorders, memory disorders, Parkinson's disease, amyotrophic lateral sclerosis, Alzheimer's disease, Huntington's disease, bulimia, anorexia nervosa or other eating disorders, compulsive acts or premenstrual syndrome.

The invention furthermore relates to pharmaceutical preparations for the control of disorders of the central nervous system, comprising at least one compound of the formula I or one of its physiologically acceptable salts or solvates.

These preparations can be used as pharmaceuticals in human or veterinary medicine. Possible vehicles are organic or inorganic substances which are suitable Thor enteral (e.g. oral), or parerteral administration or topical application and do not react with the novel compounds, for example water, vegetable oils, benzyl alcohols, alkylene glycols, polyethylene glycols, glycerol triacetate, gelatin, carbohydrates such as lactose or starch, magnesium stearate, talc or petroleum jelly. Tablets, pills, coated tablets, capsules, powders, granules, syrups, juices or drops, in particular, are used for oral administration, suppositories are used for rectal administration, solutions, preferably oily or aqueous solutions, in addition suspensions, emulsions or implants, are used for parenteral administration, and ointments, creams or powders are used for topical application. The novel compounds can also be lyophilized and the lyophilizates obtained used, for example, for the production of injection preparations. The preparations indicated can be sterilized and/or can contain excipients such as lubricants, preservatives, stabilizers and/or wetting agents, emulsifiers, salts for influencing the osmotic pressure, buffer substances, colorants, flavourings and/or other active compounds, e.g. one or more vitamins.

The invention also relates to a process for the production of these pharmaceutical preparations, which is characterized in that a compound of the formula I or one of its physiologically tolerable salts or solvates is brought into a suitable dose for together with at least one solid, liquid or semiliquid vehicle or excipient and, if appropriate, in combination with one or more other active compound.

The compounds of the formula I and their physiologically acceptable salts or solvates can be employed for the control of disorders of the central nervous system.

The substances according to the invention are as a rule administered here in a dose of preferably between approximately 1 and 500 mg, in particular between 5 and 100 mg, per dose unit. The daily dose is preferably between approximately 0.02 and 10 mg/kg of body weight. The specific dose for each patient, however, depends on all sorts of, factors, for example on the efficacy of the specific compound employed, on the age, body weight, general state of health, sex, on the diet, on the time and route of administration, and on the excretion rate, pharmaceutical combination and severity of the particular disorder to which the therapy applies. Oral administration is preferred.

The following examples relate to pharmaceutical preparations:

EXAMPLE A

Injection vials

A solution of 100 g of an active compound of the formula I and 5 g of disodium hydrogerphosphate is adjusted to pH 6.5 in 3 l of double-distilled water using 2N hydrochloric acid, sterile-filtered, filled into injection vials, lyophilized under sterile conditions and aseptically sealed. Each injection vial contains 5 mg of active compound.

EXAMPLE B

Suppositories

A mixture of 20 g of an active compound of the formula I is fused with 100 g of soya lecithin and 1400 g of cocoa butter, poured into moulds and allowed to cool, Each suppository contains 20 mg of active compound.

EXAMPLE C

Solution

A solution of 1 g of an active compound of the formula I, 9.38 g of $NaH_2PO_4.2 H_2O$, 28.48 g of $Na_2HPO_4.12 H_2O$ and 0.1 g of benzalkonium chloride in 940 ml of double-distilled water is prepared. It is adjusted to pH 6.8, made up to 1 l and sterilizes by irradiation. This solution can be used in the form of eye drops.

EXAMPLE D

Ointment 500 mg of an active compound of the formula I are mixed with 99.5 g of petroleum jelly under aseptic conditions

EXAMPLE E

Tablets

A mixture of 1 kg of active compound of the formula I, 4 kg of lactose, 1.2 kg of potato starch, 0.2 g of talc and 0.1 kg of magnesium stearate is compressed to give tablets in a customary manner such that each tablet contains 10 mg of active compound.

EXAMPLE F

Coated tablets

Analogously to Example E, tablets are pressed sad are then coated in a customary manner with a coating of sucrose, potato starch, talc, tragacanth and colorant.

EXAMPLE G

Capsules 2 kg of active compound of the formula I are filled into hard gelatin capsules in a customary manner such that each capsule contains 20 mg of the active compound.

EXAMPLE H

Ampoules

A solution of 1 kg of active compound of the formula I in 60 ml of double-distilled water is sterile-filtered, filled into ampoules, lyophilized under sterile conditions and aseptically sealed. Each ampoule contains 10 mg of active compound.

What is claimed is:

1. A compound of formula I'

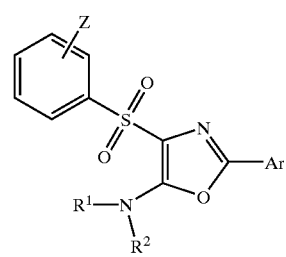

in, which $R^1$, $R^2$ each independently of one another are H, A, $—(CH_2)_n—Ar$ or alkenyl having 2 to 6 atoms, $R^1$ and $R^2$ together are also a mononuclear saturated heterocycle having 1 or 2 N, O and/or S atoms, Z is $CF_3$, $NO_2$, Hal, OH, $NH_2$, NHA or $NA_2$, A is alkyl having 1 to 6 C atoms, Ar is phenyl which is mono- or disubstituted by Z, Hal is F, Cl, Br or I, n is 1 or 2 or a physiologically acceptable salt or solvate thereof.

2. A method for treating a disorder of the central nervous system, comprising administering an effective amount of a compound of formula I to a patient in need thereof

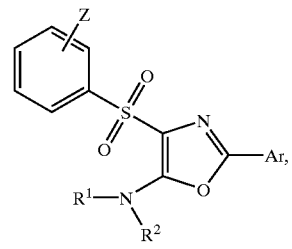

in, which $R^1$, $R^2$ each independently of one another are H, A, $—(CH_2)_n—Ar$ or alkenyl having 2 to 6 atoms, R$^1$ and R$^2$ together are also a mononuclear saturated heterocycle having 1 or 2 N, O and/or S atoms, Z is H, A, CF$_3$, NO$_2$, Hal, OH, NH$_2$, NHA or NA$_2$, A is alkyl having 1 to 6 C atoms, Ar is phenyl which is mono- or disubstituted by Z, Hal is F, Cl, Br or I, n is 1 or 2.

3. A method for the treatment of psychoses, schizophrenia, manic depression, depression, neurological disorders, memory disorders, Parkinson's disease, amyotrophic lateral sclerosis, Alzheimer's disease, Huntington's disease, bulimia, anorexia nervosa, eating disorders, compulsive acts or premenstrual syndrome, comprising administering an effective amount of a compound of formula I to patient in need thereof

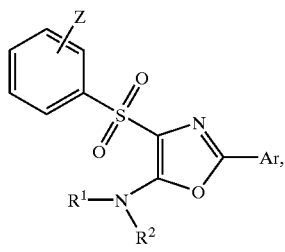

I in, which

R$^1$, R$^2$ each independently of one another are H, A, —(CH$_2$)$_n$—Ar or alkenyl having 2 to 6 atoms, R$^1$ and R$^2$ together are also a mononuclear saturated heterocycle having 1 or 2 N, O and/or S atoms, Z is H, A, CF$_3$, NO$_2$, Hal, OH, NH$_2$, NHA or NA$_2$, A is alkyl having 1 to 6 C atoms, Ar is phenyl which is mono- or disubstituted by Z, Hal is F, Cl, Br or I, n is 1 or 2.

4. A pharmaceutical composition, comprising a compound of formula I

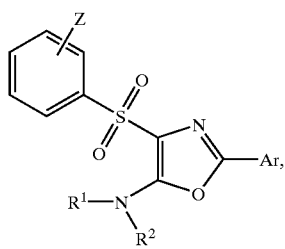

I in, which

R$^1$, R$^2$ each independently of one another are H, A, —(CH$_2$)$_n$—Ar or alkenyl having 2 to 6 atoms, R$^1$ and R$^2$ together are also a mononuclear saturated heterocycle having 1 or 2 N, O and/or S atoms, Z is H, A, CF$_3$, NO$_2$, Hal, OH, NH$_2$, NHA or NA$_2$, A is alkyl having 1 to 6 C atoms, Ar is phenyl which is mono- or disubstituted by Z, Hal is F, Cl, Br or I, n is 1 or 2 and a pharmaceutically acceptable carrier.

5. A process for the production of a pharmaceutical composition according to claim 4, comprising bringing a compound of the formula I or one of its physiologically tolerable salts or solvates into a suitable dose form together with at least one solid, liquid or semiliquid vehicle or excipient and, optionally, one or more other active compounds.

6. A method for treating a disease mediated by 5-HT6 receptors, comprising administering an effective amount of a compound of formula I to patient in need thereof

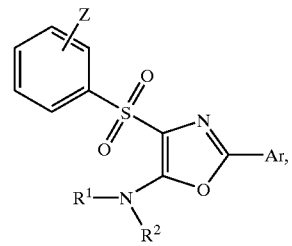

I in, which

R$^1$, R$^2$ each independently of one another are H, A, —(CH$_2$)$_n$—Ar or alkenyl having 2 to 6 atoms, R$^1$ and R$^2$ together are also a mononuclear saturated heterocycle having 1 or 2 N, O and/or S atoms, Z is H, CF$_3$, NO$_2$, Hal, OH, NH$_2$, NHA or NA$_2$, A is alkyl having 1 to 6 C atoms, Ar phenyl which is mono- or disubstituted by Z, Hal is F, Cl, Br or I, n is 1 or 2.

7. A method according to claim 6, comprising administering a) dimethyl-[2-phenyl-4-(toluene-4-sulfonyl)oxazol-5-yl]amine, b) [2-(2,4-dichlorophenyl)-4-(toluene-4-sulfonyl)oxazol-5-yl]dimethylamine, c) benzyl-[4-(4-cholorbenzenesulfonyl)-2-(2-chlorophenyl)oxazol-5-yl]amine, d) (4-benzenesulfonyl-2-o-tolyloxazol-5-yl)-methylamine, e) benzyl-[2-(2,4dichlorophenyl)-4-(toluene-4-sulfonyl)oxazol-5-yl]amine, f) [4-benzenusulfonyl-2-(2-,4dichlorophenyl)oxazol-5-yl]benzylamine, or g) [4-benzenusulfonyl-2-(2-,4dichlorophenyl)oxazol-5-yl]dimethylamine.

* * * * *